US008513463B2

(12) United States Patent
Claeys et al.

(10) Patent No.: US 8,513,463 B2
(45) Date of Patent: Aug. 20, 2013

(54) PROCESS FOR THE PRODUCTION OF NITROGEN OR PHOSPHORUS CONTAINING COMPOUNDS FROM SYNTHESIS GAS

(75) Inventors: Michael Christian Maximilian Claeys, Sea Point (ZA); Eric Wilhelmus Josephus Van Steen, Pinelands (ZA); Frank Roessner, Oldenburg (DE); Tawanda Stephen Sango, Cape Town (ZA)

(73) Assignees: The University of Cape Town, Cape Town (ZA); Carl Von Ossietzky Universitat Oldenburg, Oldenburg (DE)

( * ) Notice: Subject to any disclaimer, the term of this patent is extended or adjusted under 35 U.S.C. 154(b) by 286 days.

(21) Appl. No.: 12/988,052

(22) PCT Filed: Apr. 15, 2009

(86) PCT No.: PCT/IB2009/005242
§ 371 (c)(1),
(2), (4) Date: Dec. 15, 2010

(87) PCT Pub. No.: WO2009/127942
PCT Pub. Date: Oct. 22, 2009

(65) Prior Publication Data
US 2011/0092728 A1    Apr. 21, 2011

(30) Foreign Application Priority Data
Apr. 16, 2008  (ZA) .................................. 08/3393

(51) Int. Cl.
*C07C 231/00* (2006.01)
*C07C 233/00* (2006.01)
*C07F 9/02* (2006.01)

(52) U.S. Cl.
USPC ................................ 564/132; 564/215; 568/8

(58) Field of Classification Search
USPC ............................................. 564/132; 568/8
See application file for complete search history.

(56) References Cited

U.S. PATENT DOCUMENTS

| 2,821,537 A | 1/1958 | Rottig et al. |
| 3,726,926 A | 4/1973 | Brown et al. |
| 4,179,462 A | 12/1979 | Olive et al. |
| 4,272,452 A | 6/1981 | Auvil et al. |
| 4,556,734 A * | 12/1985 | Knifton .................. 564/132 |
| 4,558,157 A * | 12/1985 | Marsella et al. .......... 564/132 |
| 6,441,234 B1 * | 8/2002 | Dahlhaus et al. ........ 564/132 |
| 2005/0154069 A1 | 7/2005 | Inga et al. |

FOREIGN PATENT DOCUMENTS

| CN | 1333744 A | 1/2002 |
| DE | 904891 | 2/1954 |
| EP | 0031242 A1 | 12/1980 |
| EP | 0032623 A2 | 12/1980 |
| EP | 0032623 A3 | 12/1980 |
| JP | 57042660 A | 3/1982 |

OTHER PUBLICATIONS

European Search Report for corresponding European Application No. 097336515-1211/2274277 PCT/IB 2009005242, dated Apr. 1, 2012.
Danno S., et al., Formamide cpds. prepn. In high yield—by reacting ammonia or amine with carbon monoxide in presence of hydrogen and platinum gp. or cpd. metal catalyst; Abstract in Database WPI, Section Ch, week 198216, Thomson Scientific, London, GB, AN 1982-31689E, XP-002665858, Mar. 10, 1982.
Chinese Office Action issued Jan. 5, 2013 in corresponding Chinese Patent Application No. 200980113744.1.
Kolbel, H., and Ralek M 1984, "The Kolbel-Engelhardt Synthesis" in R.B. Anderson (ed), The Fischer-Tropsch Synthesis, Acedemic Press, pp. 287-288.
International Search Report for corresponding PCT Application No. PCT/IB2009/005242, dated Apr. 13, 2010.

* cited by examiner

*Primary Examiner* — Johann R Richter
*Assistant Examiner* — Kofi Adzamli
(74) *Attorney, Agent, or Firm* — Caesar, Rivise, Bernstein, Cohen & Pokotilow, Ltd.

(57) ABSTRACT

A process is described for the production of one or more of linear nitriles, amides and formamides which includes reacting a nitrogen containing compound, such as ammonia or $NO_x$, and a synthesis gas over a catalyst at a temperature of between 160° C. and 400° C. and a pressure of between 1 bar and 50 bar. A further process for the production of one or more of linear phosphorous containing compounds is also described, which includes reacting a phosphorous containing compound, such as a phosphine, and a synthesis gas over a catalyst at a temperature of between 160° C. and 400° C. and a pressure of between 1 bar and 50 bar. A supported cobalt, iron, ruthenium or rhodium catalyst or an unsupported (bulk) promoted iron catalyst, modified with a promoter is used. The synthesis gas is a mixture of hydrogen and carbon monoxide, in a ratio from 0.5:1 to 5:1; or a mixture of hydrogen and carbon dioxide; or a mixture of water and carbon monoxide. The suppression of the formation of oxygenates in the process is a feature of the invention and oxygenates may even be included in the feed to become converted to corresponding nitrogen containing compounds in the process.

15 Claims, No Drawings

PROCESS FOR THE PRODUCTION OF NITROGEN OR PHOSPHORUS CONTAINING COMPOUNDS FROM SYNTHESIS GAS

FIELD OF THE INVENTION

This invention relates to a process for the production of hydrocarbons from synthesis gas and, more particularly, to a process in which the production of nitrogen or phosphorus containing compounds such as linear nitriles, amides, formamides and linear phosphorous containing compounds during the relevant reactions of carbon oxides is enhanced.

BACKGROUND TO THE INVENTION

Fischer-Tropsch carbon monoxide hydrogenation is a catalysed process in which a carbon monoxide and hydrogen mixture, typically referred to a "synthesis gas" or "syngas", is converted into liquid hydrocarbons, predominantly linear hydrocarbons (olefins and paraffins) of different chain length. Small amounts of oxygenates, mainly alcohols, aldehydes and acids can also be formed. The products can be used to produce transportation fuels such as diesel and petrol as well as waxes. Alternately, or in addition, valuable chemicals such as olefins and oxygenates can be extracted from the product.

The synthesis gas can include carbon dioxide instead of carbon monoxide and water instead of hydrogen, and may alternatively include combinations of these reactants.

Literature from the 1960's and 1970's suggests that linear primary amines may be formed upon co-feeding of ammonia and other nitrogen-containing compounds to the synthesis gas during Fischer-Tropsch synthesis or other reactions involving synthesis gas. This may be a result of using iron based catalysts prevalent at the time as iron is known to catalyse ammonia production. Thus Kölbel H., Abdulahad I., Ralek M. Erdöl Kohle 28 (1975) 385 showed that the addition of ammonia or amines to Fischer-Tropsch synthesis gas results in the formation of higher alkyl substituted amines.

DE904891 describes adding of ammonia (1.3 Vol. %) to Fischer-Tropsch synthesis gas (CO:H2=1:1) and reacting over a copper or alkali promoted fused iron catalyst to yield up to 18 wt. % nitrogen containing compounds in the liquid product, primarily in the form of amines.

U.S. Pat. No. 2,821,537 describes the addition of ammonia or methylamine during Fischer-Tropsch synthesis over potassium promoted precipitated iron catalyst. Addition of up to 2 vol % ammonia at 30 bar and 190 to 210° C. led to formation of 10-20 wt % nitrogen containing compounds with primary linear amines making up the bulk of these.

U.S. Pat. No. 3,726,926 discloses the formation of linear alkylamines of chain length 3-22 with a selectivity of 20 to 40 wt % during Fischer-Tropsch synthesis with ammonia addition to $H_2$ and CO over group VIII metal, supplemented by smaller amounts of group III and group IA and IIA metals at conditions ranging from 160-220° C. and 50-200 bar. Typical feed composition ratios of $NH_3$:CO:$H_2$ were 0.03-0.5:0.8-1.2:1-3.

U.S. Pat. No. 4,272,452 discloses a process for the preparation of acetonitrile ($CH_3CN$), a very short chain nitrile, from CO, $H_2$ and ammonia at high temperatures (350-600° C.) over transition metals such as molybdenum and iron. These are not Fischer-Tropsch reactions conditions.

Kölbel, H., and Ralek M 1984, 'The Kölbel-Engelhardt Synthesis' in R. B. Anderson (ed), The Fischer-Tropsch Synthesis, Academic Press, pp. 287-288 discloses the formation of primary aliphatic amines ($C_1$-$C_{20}$) to up to 25 wt. % of total product from a CO, $H_2O$ and ammonia feed. It is further reported that higher partial pressure of ammonia results in shorter hydrocarbon chains of the amines formed. Typical catalysts used were precipitated iron bulk catalyst promoted with 0.2 wt. % Cu and 0.6 wt. % K. Typical reaction conditions were 11 bar and 219-235° C. No formation of nitriles or amides is reported in this document and the use of a slurry reactor as opposed to a fixed-bed reactor was reported to be unfavourable.

More recently, cobalt based catalysts have become an alternative to iron based catalysts as the most widely used in Fischer-Tropsch reactions and studies have found that nitrogen and nitrogen containing products act as a poison to these catalysts. Thus, whilst it is highly desirable to produce linear nitriles, amides and formamides from a synthesis gas feed, the prior art indicates that this is not viable as only amines are produced and as nitrogen based compounds poison cobalt based catalysts.

In this specification, linear phosphorous containing compounds shall mean organic compounds which include a phosphorous atom.

OBJECT OF THE INVENTION

It is an object of this invention to provide a process which at least partially alleviates some of the abovementioned problems.

SUMMARY OF THE INVENTION

In accordance with this invention there is provided a process for the production of at least one nitrogen or phosphorus containing compound selected from linear nitriles, amides, formamides and linear phosphorous containing compounds from synthesis gas during the hydrogenation of carbon monoxide and or carbon dioxide in a synthesis gas in a feed to a reactor in which a catalyst acts on the feed at a temperature of between 160° C. and 400° C. and under a pressure of between 1 bar and 50 bar, the process being characterized in that at least one nitrogen and phosphorous containing compound is fed to the reactor together with the synthesis gas and in that the catalyst and process conditions are selected to favour the production of said at least one nitrogen or phosphorus containing compound selected from linear nitriles, amides, formamides and linear phosphorous containing compounds.

Further features of the process provide for the catalyst to be selected for the catalyst to be selected from cobalt, iron, ruthenium and rhodium or mixtures thereof, for the catalysts to be modified with one or more promoters, but preferably unsupported promoted iron; for the iron catalyst preferably to be modified with one or more promoters including an alkali promoter such as potassium and a reduction promoter such as copper and a structural promoter such as alumina or silica; for the nitrogen containing compound to include ammonia and $NO_x$; and for the reactor to be selected from a slurry phase reactor, a fixed bed reactor and a fluidised bed reactor.

According to one aspect of the invention there is provided for the synthesis gas to be a mixture of hydrogen and carbon monoxide; and for the ratio of hydrogen to carbon monoxide to be from 0.5:1 to 5:1.

According to a second aspect of the invention there is provided for the synthesis gas to be a mixture of hydrogen and carbon dioxide.

According to a third aspect of the invention there is provided for the synthesis gas to be a mixture of water and carbon monoxide.

According to a fourth aspect of the invention there is provided for the synthesis gas to be a mixture of all of hydrogen, water, carbon monoxide and carbon dioxide.

In one variation of the invention a process for the production of one or more of linear phosphorous containing compounds includes reacting a phosphorous containing compound and a synthesis gas over the catalyst.

A further feature of this variation of the invention provides for the phosphorous containing compounds to include phosphines.

The invention also provides a process for the suppression of oxygenates formation during the hydrogenation of one of carbon monoxide or carbon dioxide in a synthesis gas which includes co-feeding a compound containing either or both of nitrogen and phosphorous with the synthesis gas to the reactor.

The oxygenates typically include alcohols, aldehydes and acids.

The hydrogenation reaction may occur as a Fischer-Tropsch reaction.

The invention still further provides a process for converting an oxygenate to a corresponding nitrogen containing compound which includes hydrogenating a feed which includes the oxygenate, a compound containing either or both of nitrogen and phosphorous and a synthesis gas over a catalyst at a temperature of between 160° C. and 400° C. and a pressure of between 1 bar and 50 bar.

DETAILED DESCRIPTION BY WAY OF AN EXAMPLE

The invention will now be further described, by way of example only. In this example a feed of a hydrogen/carbon monoxide synthesis gas and ammonia was reacted in a slurry reactor over a potassium promoted iron catalyst (mass ratios: 100 g Fe: 2 g K).

The catalyst was prepared via precipitation from aqueous iron nitrate solution using an aqueous ammonium carbonate solution. The precipitate was then dried at 120° C. and calcined under air flow at 350° C. for 4 hours. The catalyst was then promoted via incipient wetness impregnation using an aqueous potassium nitrate solution, and again dried and calcined at 350° C. for 4 hours. The catalyst was then reduced in flowing hydrogen at 350° C. for 16 hours and transferred into a slurry reactor. The reactor was maintained at a temperature at 250° C. and a synthesis gas pressure of 5 bar, with a fixed synthesis gas flow rate of $H_2$:CO (2:1) of 75 ml(n)/min. The ammonia was added to the synthesis gas at different levels, the total pressure was raised accordingly so that partial pressures of $H_2$ and CO did not change during the series of experiments. The following ammonia feeds were used:

| Ammonia in feed (%) | Reactor pressure (bar) | Ammonia partial pressure in feed (bar) |
|---|---|---|
| 0 | 5.0 | 0 |
| 2 | 5.1 | 0.1 |
| 5 | 5.3 | 0.3 |
| 10 | 5.6 | 0.6 |
| 20 | 6.3 | 1.3 |

It was found that the conversion of synthesis gas decreased slightly from 45% to 30% during the experiments. An analysis of the products obtained from the reactions is shown in Table 1 (see page 8). No changes in methane selectivity and chain growth probability were observed upon addition of ammonia.

The formation of nitrogen containing compounds was confirmed by means of gas chromatograph (GC)/mass spectrometer (MS) detection. As reported in the prior art, linear amines were formed (up to 6.6%, carbon number $C_2$ to $C_{12}$). According to the invention, however, long chain nitriles (carbon numbers $C_2$ to $C_{20}$) were also formed with these totaling up to 4.3% of the compounds formed.

Small amounts of linear amides and formamides were also detected. These have not reported in the prior art for this type of reaction.

The addition of ammonia led to a significant decrease of levels of alcohols and aldehydes. This suggests that these may be involved in the reactions as precursors to the nitrogen compounds.

Importantly, the formation of acids was also seen to have been suppressed to levels that were not detectable where 5% and more ammonia was present in the synthesis gas. This is highly desirable as acids are typically not sought after in such reactions.

The formation of a white solid, possibly ammonium carbonate, was observed in experiments with high levels of ammonia in the feed gas.

The process of the invention allows valuable nitrogen compounds, particularly nitriles, amides and formamides, to be obtained in a relatively simple and cost-effective manner from a Fischer-Tropsch reaction whilst having little effect on the overall result of the process.

The process also lends itself to both suppressing oxygenate formation and to converting oxygenates, such as alcohols, aldehydes and acids, into corresponding nitrogen containing compounds by co-feeding the oxygenates to the reactor. This may be particularly useful in the case of glycerine which is produced in large quantities as a by-product of biodiesel production.

It will be appreciated, however, that many other embodiments of a process exist which fall within the scope of the invention, particularly regarding the feed materials, reaction conditions, reactor type and catalyst. For example $NO_x$, being any one or more of $N_2O$, NO and $NO_2$, could be used instead of ammonia. It may have the benefit of providing similar product but with a different selectivity which may favour the production of amides.

TABLE 1

| | % Ammonia | | | | |
|---|---|---|---|---|---|
| | 0 | 2 | 5 | 10 | 20 |
| Paraffins | | | | | |
| $C_1$ | 11.8 | 14.2 | 13.4 | 13.5 | 13.4 |
| $C_2$-$C_5$ | 9.6 | 9.7 | 8.8 | 8.3 | 8.2 |
| $C_6$-$C_{12}$ | 7.1 | 6.7 | 6.6 | 6.6 | 6.7 |
| $C_{13}$-$C_{20}$ | 4.1 | 3.8 | 3.3 | 3.5 | |
| $C_1$-$C_{20}$ | 32.6 | 34.4 | 32.1 | 31.9 | 28.2 |
| Olefins | | | | | |
| $C_2$-$C_5$ | 32.5 | 36.3 | 34.1 | 32.5 | 42.4 |
| $C_6$-$C_{12}$ | 17.7 | 17.7 | 17.7 | 17.7 | 24.2 |
| $C_{13}$-$C_{20}$ | 3.9 | 4.4 | 5.0 | 5.6 | |
| $C_1$-$C_{20}$ | 54.1 | 58.3 | 56.7 | 55.8 | 66.5 |
| Alcohols | | | | | |
| $C_2$-$C_5$ | 4.3 | 0.5 | 0.4 | 1.1 | 0.9 |

TABLE 1-continued

| | % Ammonia | | | | |
|---|---|---|---|---|---|
| | 0 | 2 | 5 | 10 | 20 |
| $C_6$-$C_{12}$ | 3.3 | 0.8 | 0.8 | 0.5 | 0.1 |
| $C_{13}$-$C_{20}$ | 0.7 | 0.2 | 0.0 | 0.3 | |
| $C_1$-$C_{20}$ Aldehydes | 8.2 | 1.5 | 1.2 | 1.9 | 1.0 |
| $C_2$-$C_5$ | 2.7 | 0.8 | 0.0 | 0.0 | 0.0 |
| $C_6$-$C_{12}$ | 2.3 | 0.4 | 0.1 | 0.1 | 0.0 |
| $C_{13}$-$C_{20}$ | | 0.0 | 0.0 | 0.0 | 0.0 |
| $C_1$-$C_{20}$ Acids | 5.0 | 1.2 | 0.2 | 0.1 | 0.0 |
| $C_2$-$C_5$ | 0.1 | 1.4 | not det | not det | not det |
| $C_6$-$C_{12}$ | | | | | |
| $C_{13}$-$C_{20}$ | | | | | |
| $C_1$-$C_{20}$ Nitriles | 0.1 | 1.4 | not det | not det | not det |
| $C_2$-$C_5$ | | 0.7 | 0.5 | 0.8 | |
| $C_6$-$C_{12}$ | | 0.7 | 2.5 | 2.0 | 4.3 |
| $C_{13}$-$C_{20}$ | | 0.1 | 0.1 | 0.3 | |
| $C_1$-$C_{20}$ Amines (primary) | | 1.5 | 3.1 | 3.0 | 4.3 |
| $C_2$-$C_5$ | | 0.9 | 2.0 | 2.1 | n/a |
| $C_6$-$C_{12}$ | | 0.6 | 4.1 | 4.6 | n/a |
| $C_{13}$-$C_{20}$ | | | | | |
| $C_1$-$C_{20}$ Amides | | 1.5 | 6.1 | 6.6 | n/a |
| $C_2$-$C_5$ | | | | | |
| $C_6$-$C_{12}$ | | 0.1 | 0.3 | 0.3 | n/a |
| $C_{13}$-$C_{20}$ | | | | | |
| $C_1$-$C_{20}$ Formamides | | 0.1 | 0.3 | 0.3 | n/a |
| $C_2$-$C_5$ | | | | | |
| $C_6$-$C_{12}$ | | 0.1 | 0.3 | 0.3 | n/a |
| $C_{13}$-$C_{20}$ | | | | | |
| $C_1$-$C_{20}$ | | 0.1 | 0.3 | 0.3 | n/a |

The invention claimed is:

1. A process for the production of at least one nitrogen or phosphorus containing compound selected from linear nitriles, amides, formamides and linear phosphorous containing compounds from synthesis gas during the hydrogenation of carbon monoxide and or carbon dioxide components in a synthesis gas in a feed to a reactor in which a catalyst acts on the feed at a temperature of between 160° C. and 400° C. and under a pressure of between 1 bar and 50 bar, the process being characterized in that at least one nitrogen and phosphorous containing compound is fed to the reactor together with the synthesis gas and in that the catalyst is heterogeneous and the process conditions are selected to favour the production of said at least one nitrogen or phosphorus containing compound selected from linear nitriles, amides, formamides and linear phosphorous containing compounds.

2. A process as claimed in claim 1 in which the formation of oxygenates during the process is suppressed.

3. A process as claimed in claim 1 in which one or more oxygenates is co-fed to the reactor to become converted to one or more corresponding nitrogen containing compounds.

4. A process as claimed in claim 1 in which the catalyst is selected from cobalt, iron, ruthenium and rhodium or mixtures thereof.

5. A process as claimed in claim 4 in which the catalyst is unsupported promoted iron.

6. A process as claimed in claim 5 in which the iron catalyst is modified with one or more promoters selected from an alkali promoter, a reduction promoter and a structural promoter.

7. A process as claimed in claim 1 in which the nitrogen containing compound includes ammonia and $NO_x$.

8. A process as claimed in claim 1 in which the synthesis gas is a mixture of hydrogen and carbon monoxide.

9. A process as claimed in claim 8 in which the ratio of hydrogen to carbon monoxide is from 0.5:1 to 5:1.

10. A process as claimed in claim 1 in which the carbonaceous gas includes carbon dioxide.

11. A process as claimed in claim 1 in which the synthesis gas includes water and carbon monoxide.

12. A process as claimed in claim 1 in which one or more of linear phosphorous containing compounds is produced by reacting a phosphorous containing compound and a synthesis gas over the catalyst.

13. A process as claimed in claim 12 in which the phosphorous containing compounds include phosphines.

14. A process as claimed in claim 1 in which the oxygenates include alcohols, aldehydes and acids.

15. A process as claimed in claim 1 in which the hydrogenation reaction occurs as a Fischer-Tropsch reaction.

* * * * *